United States Patent
Toro Restrepo et al.

(10) Patent No.: US 11,653,964 B2
(45) Date of Patent: May 23, 2023

(54) PLATE BENDER FOR MANDIBULAR IMPLANTS AND BENDING PROCESS

(71) Applicant: TECHFIT DIGITAL SURGERY INC., Daytona Beach, FL (US)

(72) Inventors: Mauricio Toro Restrepo, Daytona Beach, FL (US); Santiago Restrepo Franco, Envigado Antioquia (CO); Simón Polanía Restrepo, Medellín (CO)

(73) Assignee: TECHFIT DIGITAL SURGERY INC., Daytona Beach, FL (US)

( * ) Notice: Subject to any disclaimer, the term of this patent is extended or adjusted under 35 U.S.C. 154(b) by 269 days.

(21) Appl. No.: 16/916,192

(22) Filed: Jun. 30, 2020

(65) Prior Publication Data

US 2021/0298809 A1    Sep. 30, 2021

(30) Foreign Application Priority Data

Mar. 30, 2020   (CO) .................. NC2020/0003890

(51) Int. Cl.
| | | |
|---|---|---|
| *B21D 7/00* | (2006.01) | |
| *A61B 17/88* | (2006.01) | |
| *A61B 17/80* | (2006.01) | |
| *A61F 2/28* | (2006.01) | |
| *B21D 7/12* | (2006.01) | |

(52) U.S. Cl.
CPC ...... *A61B 17/8863* (2013.01); *A61B 17/8071* (2013.01); *A61F 2/2803* (2013.01); *B21D 7/00* (2013.01); *B21D 7/12* (2013.01)

(58) Field of Classification Search
CPC . A61B 17/8863; A61B 17/8861; A61B 17/88; B21D 7/085; B21D 7/12
See application file for complete search history.

(56) References Cited

U.S. PATENT DOCUMENTS

| | | |
|---|---|---|
| 6,423,068 B1 | 7/2002 | Reisberg |
| 8,419,745 B2 | 4/2013 | Sixto, Jr. et al. |
| 9,918,762 B2 | 3/2018 | Federspiel et al. |
| 2016/0175013 A1* | 6/2016 | Redmond ............... B21D 7/14 72/14.9 |
| 2021/0387243 A1* | 12/2021 | Brochman ............ B21D 7/024 |

FOREIGN PATENT DOCUMENTS

RU        2692982 C1    6/2019

* cited by examiner

*Primary Examiner* — Amy R Sipp
(74) *Attorney, Agent, or Firm* — Schmeiser, Olsen & Watts, LLP

(57) ABSTRACT

Provided is a plate bender for mandibular implants and the method employing it, which is intended for improving the bending process of mandibular plates or implants, reducing the number of folds (bents) until obtaining the desired geometry, further reducing fatigue failures, costs and streamlining the process, by providing a high-precision, semiautomatic bender, with modular and transportable assembly.

10 Claims, 4 Drawing Sheets

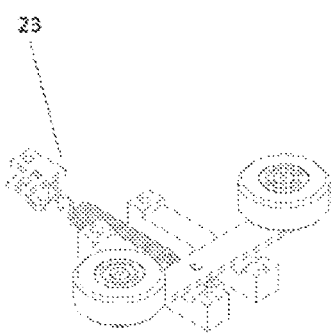
FIG. 5A
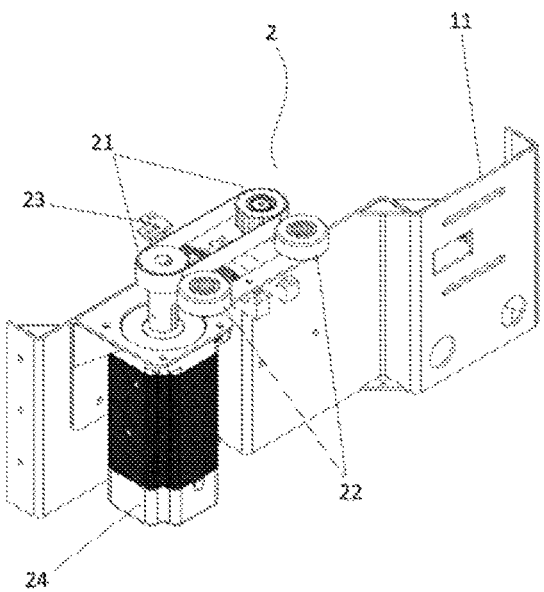
FIG. 5B
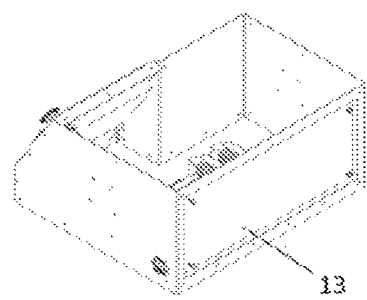
FIG. 6A
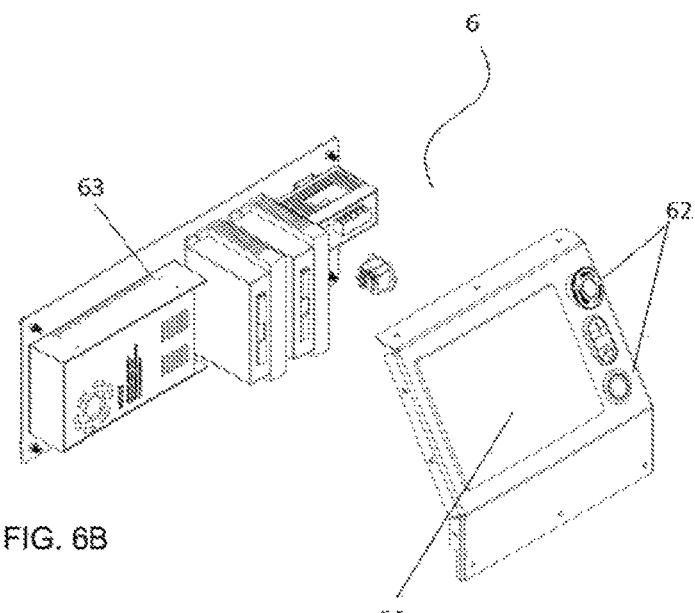
FIG. 6B
FIG. 6C

PLATE BENDER FOR MANDIBULAR IMPLANTS AND BENDING PROCESS

CROSS-REFERENCE TO RELATED APPLICATIONS

This application claims priority to Colombian Application No. NC2020/0003890, having a filing date of Mar. 30, 2020, the entire contents of which are hereby incorporated by reference.

FIELD OF TECHNOLOGY

The following relates to the field of biomedical engineering, particularly it relates to a plate bender for mandibular implants and the process employing it, which is intended for improving the bending process of mandibular plates or implants, reducing the number of folds (bents) until obtaining the desired geometry, further reducing fatigues failures, costs and streamlining the process, by providing a high-precision, semiautomatic bender, with modular and transportable assembly.

BACKGROUND

In treating mandibular fractures, it is common the use of plates for fixating the portions of fractured bone, this is how the plates should be bent by surgeons at the moment of intervention, in order to achieve a proper fit to the patient bone. However, the bending process usually subjects the plate to more than one fold in the bending (folding) points, causing thereby loss of the mechanical properties of the plate due to fatigue.

In addition, the time invested and the bending process during surgery propitiate possible infections in the patient and delays in surgeries.

There is a plurality of disclosures in the state of the art which propose different solutions to the technical problem indicated, such as document U.S. Pat. No. 9,918,762B2, which presents, a system including methods and apparatus, for deforming a plate member on bone. In some embodiments, the system may comprise a plate member defining a plurality of openings to receive fasteners that attach the plate member to the bone. The plate member may include a pair of undercut flanges formed by opposite edge regions of the plate member. The system also may comprise a bending tool configured to be operatively associated with the plate member after the plate member is attached to bone, with a region of the bending tool positioned under each of the undercut flanges, such that rotation of the bending tool applies a moment to the plate member.

However, the invention defined in this anteriority features the disadvantage that the plate bending is performed manually, on the bone, without including any element which guarantees a final bending angle.

On the other hand, document U.S. Pat. No. 8,419,745B2 discloses a pair of plate benders for bending a bone plate. Each bender includes a lever arm having a first end and a second end. The first end includes a fulcrum for placement on the upper surface of the plate, and a foot insertable through the oblong screw hole to contact the lower surface of the plate. The second end includes a cut-out with a central divider. The cut-out has a length dimensioned to extend widthwise about the plate at the location of the oblong screw hole with the divider extending into the oblong screw hole for stability. The second end may also be provided with a deep slot that accommodates the thickness of the plate. In use, plate benders with such structure can be used in pairs to longitudinal bend the plate; bend the plate in plane; or twist the plate along its axis.

However, the invention defined in this anteriority features the disadvantage that the plate bending is performed manually, and does not include any element which guarantees a final bending angle either.

In the state of the art, document U.S. Pat. No. 6,423,068 can also be found, which refers to an apparatus for osteosynthesis of a mandible, wherein the apparatus contains an elongated plate having a plurality of apertures, and the plate has a first portion, a second portion, and a central portion intermediate the first and second portions. Each of the apertures within the first portion and within the second portion are disposed in relatively close spaced relationship. The width of the plate between apertures is less in the central portion than in the first portion, and it can be bent to a relatively small radius in the central portion without distorting the apertures within the central portion. The invention also refers to a method for surgically preparing a mandible, which in its steps includes bending the plate to substantially conform to the mandible such that the central portion thereof overlies the symphysis of the mandible.

However, the anteriority does not specifically mention the way how the plate bending is carried out, but it just limits to indicate that, in a step of the method, the plate is bent.

On its part, document RU2692982, which relates to a procedure for maxillofacial surgery, wherein the surgical procedure is performed through a bone graft using surgical templates with guide channels for drilling a series of screw holes, wherein the method comprises making a stereolithography model, bending reconstructive plate, manufacturing the model with transplant, attaching the bent plate to the stereolithographic model, determining the position of holes in in computer tomography (CT) with further reconstruction in a 3D program, transmitting data on the position of the screws on the plates, and finally placing the graft in the patient mandible.

However, it should be noted that the anteriority does not disclose all the characteristics of embodiments of the invention since it just limits to indicated that in the surgical method one of the steps is bending the plate with the graft, but it does not specify the way how the bending is performed or the device or method used for carrying out the plate bending, which is the basis for the present development.

According to the above, it is clear that there is a need in the state of the art to design plate bender for mandibular implants which allows to obtain a plate bent customized to the patient, with the less number of operations necessary, in a precise and automatic manner, guaranteeing the desired output angles, avoiding fatigue failures and providing a final product with improved mechanical properties.

SUMMARY

An aspect relates to an electronically assisted plate bender for performing punctual angulations and deformations on a mandibular plate, avoiding as much the human intervention and guaranteeing a high-quality standard.

Another aspect of embodiments of the present invention consists in providing a plate bender with modular and independent design which facilitates the assembly and disassembly process of subsystems and its respective component while being safe, simple and easy to transport.

Another of the aspects of embodiments of the present invention consists in providing a feeding system having transmission by synchronic pulleys improving the advance of the mandibular plate and thus, the accuracy on the bending process, and a transmission system for the given movable by synchronic pulleys/time ratios 2:1, increasing the torque and reducing the speed allowing a greater accuracy and bending strength, with the aid of a bending die to improve the bending conditions of this kind of titanium plates.

BRIEF DESCRIPTION

Some of the embodiments will be described in detail, with references to the following Figures, wherein like designations denote like members, wherein:

FIG. 1A corresponds to a perspective view of the plate bender in its application position, from a first angle;

FIG. 1B corresponds to a perspective view of the plate bender in its application position, from a second angle;

FIG. 2 corresponds to a view of the plate bender, without the top cover, which allows to observe the arrangement of elements inside the bender;

FIG. 5A shows a tensor;

FIG. 5B shows a feeding system with the tensor and free rollers;

FIG. 6A shows an electronic system and the electrical power supply system;

FIG. 6B shows a control unit; and

FIG. 6C shows the control unit.

DETAILED DESCRIPTION

Figure 1A:
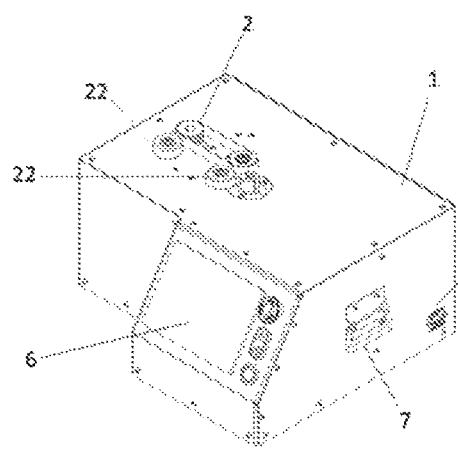
Figure 1B:
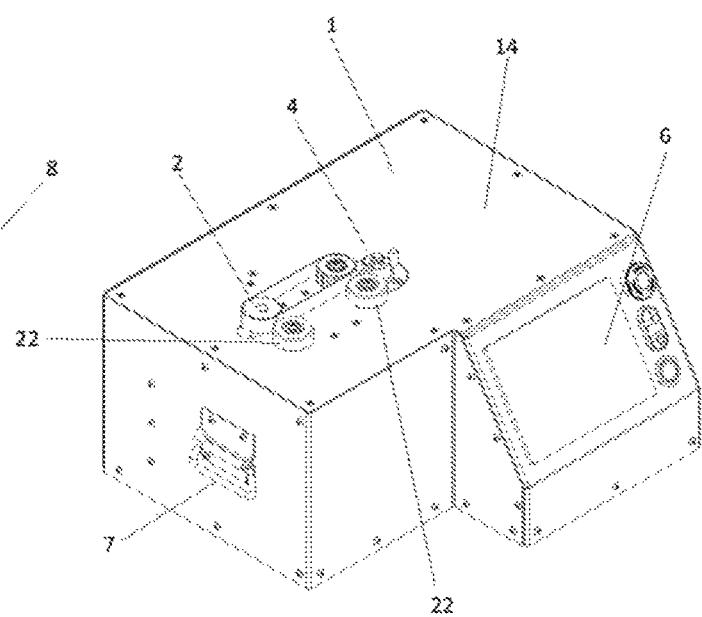
Figure 2:
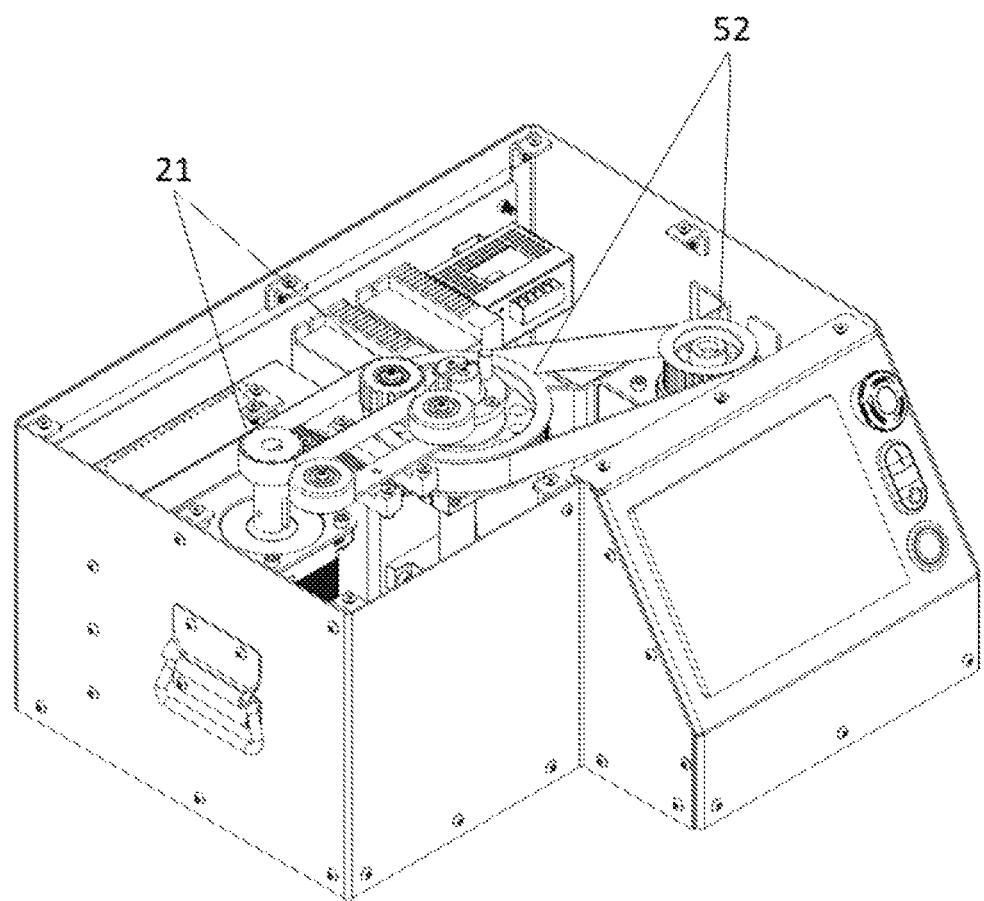
Figure 3:
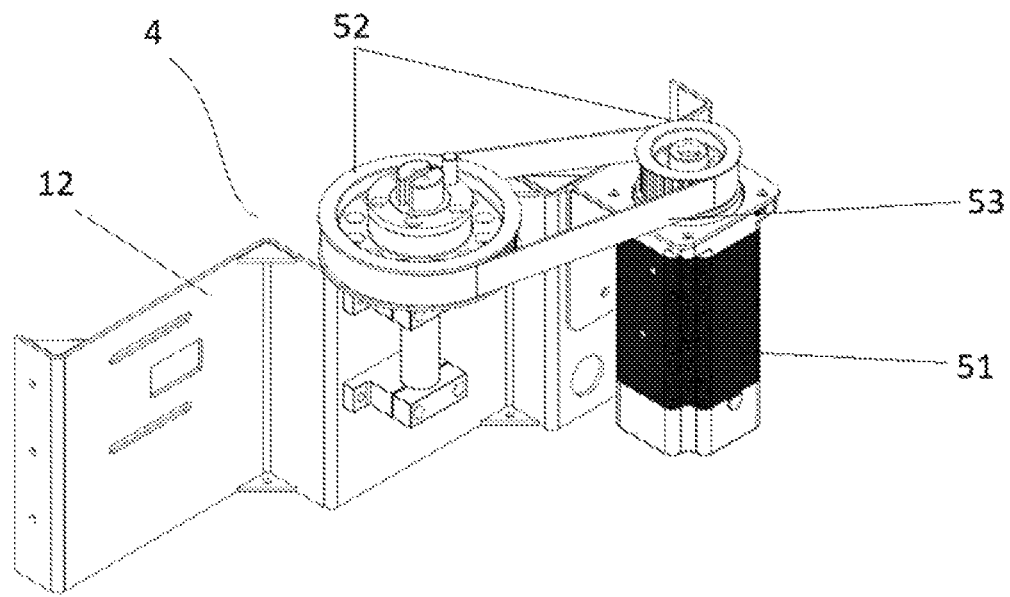
FIG. 3 shows the power unit subassembly, the bending mechanical system (bending die) and its components.
Figure 4:
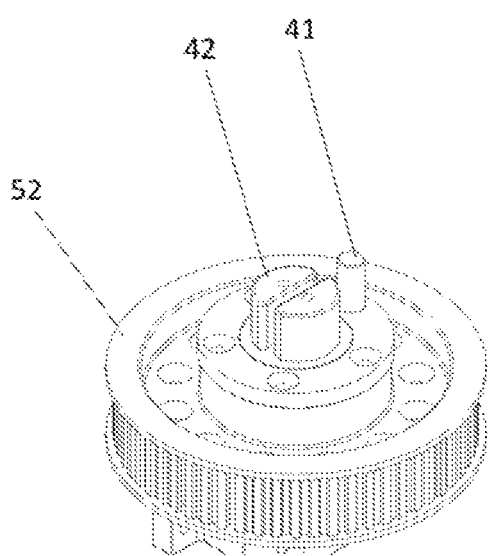
FIG. 4 shows in detail one of the synchronic pulleys and the bending die dice.

Embodiments of the present invention is directed to a plate bender for mandibular implants, comprising the following components:

Referring to FIGS. 1A-6C, plate bender for mandibular implants comprising a support structure (1), a feeding system (2), a clamping mechanism (22) which fastens the pate or mandibular implant in a specific position, a bending die system (4), a power unit (5), a control unit (6), and an output platform.

The feeding system (2) comprises an advance mechanism by synchronic pulleys (21), operated by a feeding servo (24), a free roller mechanism (22) connected to a tensor mechanism (23) which improves the advancement and position of the mandibular plate and thus, the bending accuracy, wherein the elements are supported on the modular structure (11) of the feeding system.

In addition, the bending die system (4) comprises a fixed pin (42), a movable pin (41) of angular oscillation, wherein the movable pin receives the specific rotation power and angle by a power transmission system (52) formed by synchronic pulleys in transmission ratio 2:1, and a toothed belt (53), operated by the servo (51).

On its part, the control unit (6) comprises a mixed system formed by a touch controller (61) and auxiliary buttons (62) to facilitate its operation by the operator, wherein the electrical system (63) is located on one side of the support structure (1), side on which the 110V with integrated fuse charge or electrical power supply system (8) is located. On its part, the 48V 10 Ah power source feeds the electronic circuitry and the control system.

The support structure (1) is configured on a modular manner to facilitate the maintenance of each of the elements and comprises the modular structure (11) of the feeding system, the modular structure (12) of the power system, the transportation handles (7), and the covers (13), (14), which are easy to remove for maintenance, its attachment could be made through screws, allowing that both the electrical and mechanical reparations can be performed with minimal disassembly.

The feed from the platform to the fastening and bending mechanism can be mechanical or automatic.

Finally, embodiments of the present invention also comprises a method for bending mandibular implants, characterized by comprising the following steps:
  Entering plate bending position and angle data, according to the virtual surgical planning data.
  Positioning the mandibular implant on the feeding platform, mechanically or automatically.
  Starting the bending the process by activating the plate bender for mandibular implants, and
  Removing the bent piece.

The method is further characterized in that the bending step is automatic, reducing the number of folds and increasing the accuracy of the bent product.

On its part, the plate or mandibular implant feeding and positioning process can be made mechanically or automatically.

Although the present invention has been disclosed in the form of preferred embodiments and variations thereon, it will be understood that numerous additional modifications and variations could be made thereto without departing from the scope of the invention.

For the sake of clarity, it is to be understood that the use of "a" or "an" throughout this application does not exclude a plurality, and "comprising" does not exclude other steps or elements.

The invention claimed is:

1. A plate bender for mandibular implants comprising:
  a support structure;
  a feeding system including synchronic pulleys having a flexible belt, and free rollers positioned proximate the synchronic pulleys, wherein the synchronic pulleys and the free rollers act in concert to clamp a mandibular plate in a position and also to advance the mandibular plate through the plate bender, the flexible belt of the synchronic pulleys configured to engage the mandibular plate as the mandibular plate advances through the plate bender; and
  a bending die system positioned proximate the feeding system, the bending die system including a fixed pin and a movable pin of angular oscillation, the fixed pin having a slot therethrough to receive the mandibular plate as the mandibular plate is advanced through the plate bender, the movable pin being concentric and movable with respect to the fixed pin to change a shape of the mandibular plate as the mandibular plate is advanced through the slot of the fixed pin, wherein the movable pin is moved by a power transmission system housed within the support structure, the power transmission system moving the movable pin around the fixed pin according to a specific rotation power and angle to change the shape of the mandibular plate;
  wherein the shape of the mandibular plate formed by the plate bender is based on virtual surgical planning data.

2. The plate bender for mandibular implants according to claim 1, wherein the synchronic pulleys are operated by a feeding servo, and the free rollers are connected to a tensor mechanism controlling advancement of the mandibular plate and bending accuracy, wherein the elements are supported on a modular structure of the feeding system.

3. The plate bender for mandibular implants according to claim 1, wherein the power transmission system comprises at least one of a synchronic pulleys and a belt, the synchronic pulleys of the power transmission system being controlled by a servo.

4. The plate bender for mandibular implants claim 1, wherein the power transmission unit has a ratio of 2:1.

5. The plate bender for mandibular implants according to claim 1, further comprising a control unit comprising a touch controller and auxiliary buttons.

6. The plate bender for mandibular implants according to claim 1, wherein the support structure has transportation handles.

7. The plate bender for mandibular implants according to claim 1, further comprising an electrical charge or power supply system.

8. The plate bender for mandibular implants according to claim 1, wherein the support structure comprises covers for modular maintenance.

9. The plate bender for mandibular implants according to claim 1, wherein the mandibular plate is mechanically advanced from the feeding mechanism to the bending die system.

10. The plate bender for mandibular implants according to claim 1, wherein the mandibular plate is automatically advanced from the feeding mechanism to the bending die system.

* * * * *